United States Patent [19]

De Canto

[11] Patent Number: 4,832,030

[45] Date of Patent: May 23, 1989

[54] COLLAR APPARATUS FOR RETAINING A HOT OR COLD PACK INSERT

[76] Inventor: Anthony De Canto, 349 Rte. 208 South, Somerville, N.J. 08876

[21] Appl. No.: 83,204

[22] Filed: Aug. 10, 1987

[51] Int. Cl.$^4$ .............................................. A61N 1/00
[52] U.S. Cl. .................................... 128/380; 128/402; 128/403
[58] Field of Search ....................... 128/402, 403, 380; 307/296 R

[56] References Cited

U.S. PATENT DOCUMENTS

| | | | |
|---|---|---|---|
| 4,081,150 | 3/1978 | Tyson | 128/403 |
| 4,107,509 | 8/1978 | Scher et al. | 128/402 |
| 4,576,169 | 3/1986 | Williams | 128/402 |

*Primary Examiner*—Stephen F. Husar
*Assistant Examiner*—Sue Hagarman
*Attorney, Agent, or Firm*—Arthur L. Plevy

[57] ABSTRACT

There is disclosed a collar apparatus for retaining a hot or cold pack insert. The collar apparatus comprises an elongated integral planar member fabricated from elastomeric material and having an extensive central portion including a rectangular aperture dimensioned to accommodate the hot or cold pack insert. The central portion is coextensive with right and left ends, each of which has located thereon coacting retaining means to enable the planar member to encircle the neck of a user and a tubular stocking member adapted to cover the central portion when the aperture is accommodating said insert with said stocking member adapted to encircle and central portion of said elongated planar member.

6 Claims, 1 Drawing Sheet

COLLAR APPARATUS FOR RETAINING A HOT OR COLD PACK INSERT

BACKGROUND OF THE INVENTION

This invention relates to a collar apparatus and more particularly to an improved collar apparatus which is capable of retaining a hot or cold pack insert, which collar apparatus is utilized in conjunction with a cover stocking member.

As one can well ascertain, applying heat and cold packs to areas of the body that have received injury is a common method of treatment. Such heat and cold packs are utilized extensively in conjunction with the neck area of a person due to the fact that the neck area is often times injured and the person experiences severe pain. In any event, it is desirable to maintain the application of heat or cold for a substantial period of time such as for a few hours. Hence, it is desirable to maintain the heat or cold pack in a fixed position while such heat or cold is being applied to the neck area of the person.

The prior art is aware of many devices which have been formulated to accommodate or hold heat or cold packs on various body portions of a patient or other individual. In regard to this, there are many patents which exist in the prior art which serve to provide such a function. Reference is therefore made to U.S. Pat. No. 4,576,169 issued on Mar. 18, 1986 to A. J. Williams and entitled "Comfort Collar". This patent shows a collar which can be worn around the neck of an individual to cool the individual. The packet contains an outer surface which is fabricated from a towel-like material. The pack has an insert cavity into which a suitable material is placed, such as a hot or cold pack.

U.S. Pat. No. 4,586,506 issued on May 6, 1986 to B. K. Nangle and is entitled "Elastic Wrap Connecting With Heat or Cold Pack". This patent employs an elastic wrap which includes a container for holding a heat or cold pack. The container is a fixed receptacle which contains the heat or cold pack which is inserted therein.

U.S. Pat. No. 4,625,729 issued on Dec. 2, 1986 to L. Y. Roney and entitled "Body Cooling Cuff". This patent shows a cuff-like device which has a recess or pocket for containing a heat pack 25.

See also U.S. Pat. No. 4,645,498 issued on Feb. 24, 1987 to I. Kosak and entitled "Hot Or Cold Compress With Bladder Enclosure". This patent shows a compress structure which again is used to contain a wet compress or hot towel which is placed within a suitable cavity. The compress is formed from a pair of rectangularly shaped waterproof panels which are joined together around their peripheries to form a hollow space therebetween. One of the panels has an elongated opening to allow for the introduction of ice, hot water, wet towel or the like and also carries a closure flap for closing the opening. The other panel has a portion formed of a porous fabric material so that the liquid from the hollow space can seep therethrough.

In any event, the above-noted prior art devices and other devices are extremely complicated and difficult to fabricate. Fabrication of such devices, according to the prior art, requires the formation of various seams in order to provide the apparatus shown. Other devices provide and require the formation of various pocket or insert devices. Hence, as one can ascertain, such devices, while accomplishing the desired results of holding a hot or cold pack in position, are complicated and require excessive manufacturing and fabrication time. A further disadvantage of many of the prior art devices is that they are not suitable for holding heat or cold packs and, further, are not comfortable when worn.

As indicated, the above-cited references are typical of the type of prior art devices which exist and which require extensive manufacturing procedures in order to produce such a device. Based on such operations, the devices are relatively flimsy and, hence, are not capable of being utilized a great number of times.

It is therefore an object of the present invention to provide an improved apparatus which is simple and economical to manufacture and which is comfortable to wear.

The device to be described, essentially, will accommodate a hot or cold pack in a simple and efficient manner and is an extremely rugged device which can be utilized a great number of times by a patient or individual.

BRIEF DESCRIPTION OF PREFERRED EMBODIMENT

A collar apparatus for retaining a hot or cold pack insert, said pack insert being a thermal retaining material of a rectangular configuration comprising an elongated integral planar member fabricated from an elastomeric material and having an extensive central portion including a rectangular aperture dimensioned to accommodate said rectangular pack insert with said central portion coextensive with a right and left end each of which has located thereon coacting retaining means to enable said planar member to encircle the neck of a user, and a tubular stocking member adapted to cover said central portion when said aperture is accommodating said insert.

DETAILED DESCRIPTION

Figure 1:
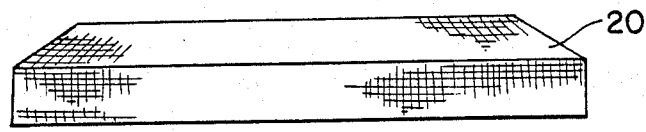
FIG. 1 is a perspective plan view of a hot or cold pack insert utilized in accordance with this invention.

Referring to FIG. 1 there is shown a typical hot or cold pack insert 20. Such inserts 20 are widely available in the prior art and essentially contain materials which can maintain a cold or a hot temperature over a prolonged period. Such cold packs or hot packs, as indicated, are available from many sources. Essentially the hot or cold pack 20 constitutes a rectangular member and is made from a material which is capable of maintaining a cold or hot temperature for a sufficient period. See for example, U.S. Pat. No. 3,804,077, issued on Apr. 16, 1974 to V. L. Williams and entitled "Hot or Cold Pack". That patent describes a hot or cold pack which is provided in which two materials are normally separated from each other in separate compartments and which the materials are mixed to produce a chemical reaction. In any event, such hot or cold packs are also available to various configurations and contain suitable thermal responding materials to enable heat or cold to be maintained for prolonged periods.

Figure 2:
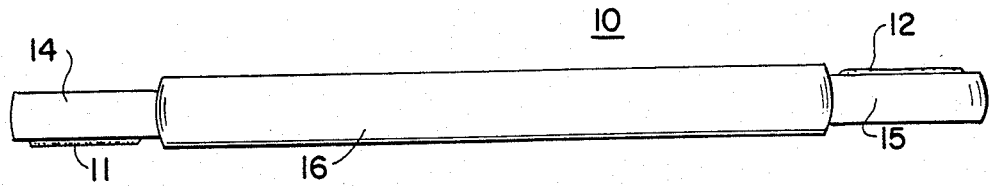
FIG. 2 is a top view of a collar device fabricated according to this invention.

Referring to FIG. 2 there is shown a top view of a collar device which will accommodate the hot or cold pack 20 of FIG. 1. As seen from FIG. 2, the device 10 is an elongated planar member which is integrally formed. The device has a central portion 16 which, as will be explained in conjunction with FIG. 3, has an insert accommodating aperture 21. The device has two end portions integrally formed with the center portion 16 as end portions 14 and 15. End portion 15 accommodates a suitable Velcro surface 12 which coacts with a Velcro accommodating surface 11 on end section 14. There are, of course, other means for securing the end portions together, such as straps, bands, and so on.

Figure 3:
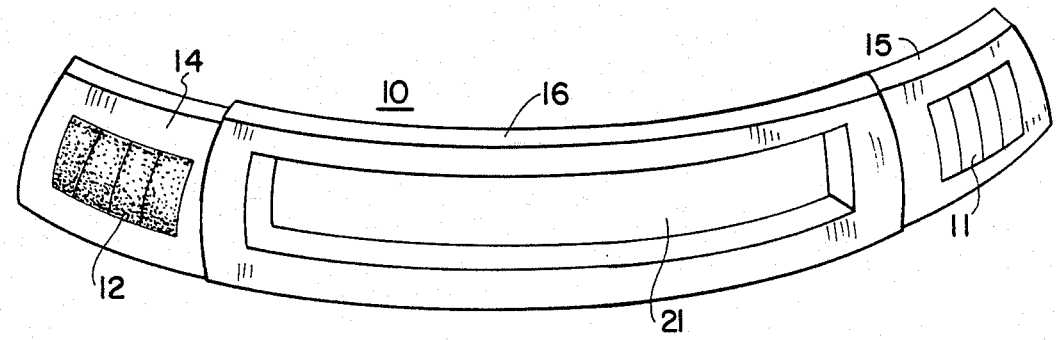
FIG. 3 is a front view of the collar device depicted in FIG. 2.

As shown in FIG. 3, there is a central aperture 21 which is formed in the central portion 16 of the integral member 10. The aperture 21 is dimensioned to accommodate the heat or cold pack. Essentially, the heat or cold pack 20, as shown in FIG. 1, is rectangular in configuration and basically is approximately the same dimensions as aperture 21. In any event, the entire member 10 is fabricated from an elastomeric material, such as a relatively soft rubber, a flexible plastic or other elastomeric material. Hence, the aperture 21 is made slightly less in area than the actual area of the hot or cold pack 20. In this manner the hot or cold pack is held in form alignment with the aperture 21 when inserted therein. The friction provided between the elastomeric surfaces of the device 10 and the hot or cold pack firmly secure the same and based on dimensions the insert 20 is accommodated totally within the aperture 21 associated with the elastomeric member 10.

Figure 4:
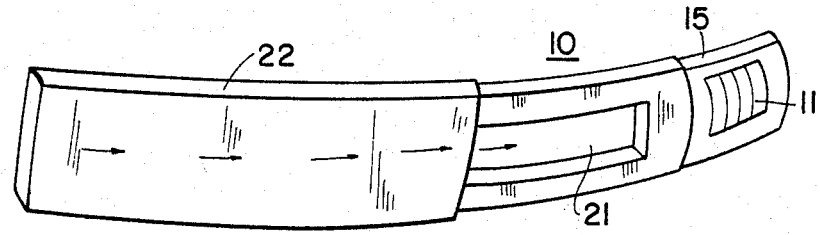
FIG. 4 is a front view showing the collar device having a stocking member 22 inserted thereover.

As seen from FIG. 4, after insertion of the pack 20 into the aperture 21 a tubular stocking member 22 is then directed over the surface of the collar device which member 22 completely surrounds the insert and the aperture 21.

Figure 5:
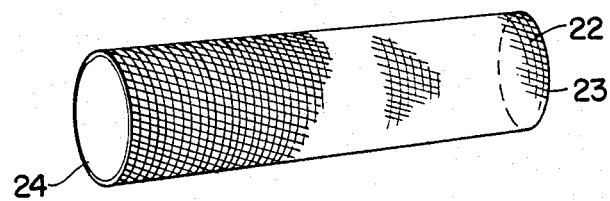
FIG. 5 is a perspective plan view of a typical stocking or cover member 22.

FIG. 5 shows a plan view of the stocking member 22. The stocking member 22 is a tubular member made of a fiber as cotton or a towel-like material and has a band 22 of elastomeric material at one end and a corresponding band 23 at the other end. In this manner the stocking, when emplaced over the elastomeric member 10, is firmly held by the bands 23 and 24 in position to completely cover the insert 20 as secured within the aperture 21. The entire unit, by means of the Velcro fasteners 11 and 12, is then wrapped or placed about the neck or other body part of an individual. In this manner the individual can assure that the heat or cold is fully impressed upon the affected area and will remain in position for the requisite period.

It is understood that the Velcro coupling devices 11 and 12 are provided in proper lengths to accommodate various neck sizes, for example, and to enable one to utilize the device in conjunction with various other body parts. Thus, the above-noted device is an extremely economical device which essentially consists of an integral piece of elastomeric material which contains a central aperture for accommodating a heat pack. The heat pack or cold pack, such as 20, is held in position within the aperture by means of the fact that the elastomeric material forming the collar device 10 will expand and will then contract to firmly hold the pack in a desired position. It is understood, of course, that the heat or cold pack 20 is also a flexible material and may, for example, consist of a cloth covering of a rectangular configuration or an integral piece of thermal responding material, as well known in the art.

Hence, as one can ascertain, the above-noted structure is extremely simple to fabricate and is extremely comfortable when worn about the neck or other body parts of a subject.

What is claimed is:

1. A collar apparatus for retaining a hot or cold pack insert, said pack insert being a thermal retaining material of a rectangular configuration comprising:

an elongated integral planar member fabricated from an elastomeric material and having an extensive central portion including a rectangular aperture in said central portion and directed through said central portion and dimensioned to accommodate said rectangular pack insert with said aperture framing said pack insert and with the major surfaces of said insert exposed via said aperture with said central portion coextensive with a right and left end each of which has located thereon coacting retaining means to enable said planar member to encircle the neck of a user, and a tubular stocking member adapted to cover said central portion when said aperture is accommodating said insert.

2. The apparatus according to claim 1 wherein said stocking member is a longitudinal tubular member having first and second openings for insertion of said member about said central portion of said planar member with each opening having an elastomeric band about the periphery thereof to firmly hold said stocking member in place.

3. The apparatus according to claim 1 wherein said planar member is fabricated from a foam rubber.

4. The apparatus according to claim 1 wherein said planar member is fabricated from a plastic material.

5. The apparatus according to claim 1 wherein said retaining means comprises Velcro strips, one located on a surface of said right end and one located on a corresponding opposite surface of said left end.

6. The apparatus according to claim 1 wherein said stocking member is fabricated from a towel like material.

* * * * *